(12) United States Patent
Mains, Jr.

(10) Patent No.: US 6,444,119 B1
(45) Date of Patent: Sep. 3, 2002

(54) BILGE WATER PROCESSING SYSTEM WITH REMOTE MONITORING AND CONTROL

(76) Inventor: Gilbert L. Mains, Jr., 5344 Eagle Ridge La., Sylvania, OH (US) 43560

( * ) Notice: Subject to any disclaimer, the term of this patent is extended or adjusted under 35 U.S.C. 154(b) by 0 days.

(21) Appl. No.: 09/830,984
(22) PCT Filed: Nov. 2, 1999
(86) PCT No.: PCT/US99/25654
§ 371 (c)(1),
(2), (4) Date: May 2, 2001
(87) PCT Pub. No.: WO00/26143
PCT Pub. Date: May 11, 2000

Related U.S. Application Data
(60) Provisional application No. 60/106,704, filed on Nov. 2, 1998.

(51) Int. Cl.$^7$ .................................................. C02F 1/40
(52) U.S. Cl. .......................... 210/85; 210/86; 210/130; 210/170; 210/242.1; 210/254; 210/DIG. 5; 340/539
(58) Field of Search .............................. 210/170, 242.1, 210/85, 86, 87, 97, 923, 241, 104, DIG. 5, 416.5, 416.1, 130, 259, 294, 302; 340/539, 540

(56) References Cited

U.S. PATENT DOCUMENTS

| 4,830,757 A | 5/1989 | Lynch et al. ................. 210/742 |
| 5,006,260 A | 4/1991 | Roques et al. ............... 210/708 |
| 5,075,014 A | 12/1991 | Sullivan ...................... 210/747 |
| 5,532,679 A | 7/1996 | Baxter, Jr. ................... 340/539 |
| 5,753,108 A | 5/1998 | Haynes et al. .............. 210/122 |
| 6,171,508 B1 * | 1/2001 | Browning, Jr. |

* cited by examiner

Primary Examiner—Joseph W. Drodge
Assistant Examiner—Terry K. Cecil
(74) Attorney, Agent, or Firm—Reising, Ethington, Barnes, Kisselle, Learman & McCulloch, P.C.

(57) ABSTRACT

A shipboard system 200 to process contaminated water and exchange commands and data with a remote facility. The shipboard system includes a separation system 10, controller 202, and a communication unit 204. The separation system includes a separator 16, oil accumulator 18, coalescer 20, and a pump 24. The controller 202 is coupled to the separation system 10 and is operable to acquire data relating to processing of contaminated water and can utilize commands received by the communication system 204 to permit remote control of the separation system. The communication unit transmits the data via satellite or other wireless transmission to a command center 212. The shipboard system can also include a global position system which can be used by the controller to inhibit the discharge of contaminated liquids when the ship is in protected waters.

16 Claims, 7 Drawing Sheets

BILGE WATER PROCESSING SYSTEM WITH REMOTE MONITORING AND CONTROL

CROSS-REFERENCE TO RELATED APPLICATION

This application claims priority from PCT/US99/25654, filed Nov. 2, 1999, which claims the benefit of U.S. Provisional Application No. 60/106,704, filed Nov. 2, 1998, entitled "Shipboard Liquid Filtration System With Remote Supervisory Control and Monitoring."

FIELD OF THE INVENTION

The present invention is directed generally to separation of immiscible liquids and is particularly useful on ocean vessels for treating contaminated water to remove oils and other hydrocarbon based contaminants.

BACKGROUND OF THE INVENTION

As concern over the environmental quality of the world's oceans continues to grow, environmentalists' attention is increasingly focusing on the widespread practice within the maritime industry of dumping polluted bilge water overboard. While many countries attempt to protect against such practices by the threat of criminal penalties and fines amounting to millions of dollars, such deterrence measures are difficult to enforce and are often easily avoided by operators who travel in and out of regulated waters. Unfortunately, pumping polluted water overboard is simpler and less expensive than either cleaning the water prior to pumping overboard or holding the polluted water until arriving in port where it can be pumped to a land based water treatment facility. As a result, pumping the polluted water overboard in unprotected waters is a daily occurrence accounting for millions of gallons of polluted water being dumped into the world's oceans every year. Many land based operations also produce polluted aqueous mixtures that can have a negative environmental impact. Like the bilge water that accumulates within a ship's hull, these land based operations often produce large quantities of water contaminated with oil, fuel, and other hydrocarbon based waste.

Physical separation systems exist which can treat the water at varying levels of effectiveness and efficiency. For example, API separators, inclined separators, and weir separators can all be used to separate out some of the oils and other immiscible liquids in a supply of contaminated water. However, these systems cannot effectively remove the finer droplets of oils nor oils having a relatively neutral buoyancy. Consequently, these systems are not suitable for shipboard use since they do not produce treated water that is sufficiently clean to return to the ocean. While finer filtration elements or chemical treatments can be used to handle the smaller oil droplets, such added components can be expensive and more labor intensive to maintain. Accordingly, there exists a need for a system that can be used to decontaminate polluted water in a manner which reduces or eliminates the incentive for operators to simply dump the polluted water into the environment. Also, there exists a need for a system that can be remotely monitored and controlled in a manner that can be relied upon by governmental regulators and insurance carriers as insuring the environmental integrity of the operator's ship or land-based facility. Further-more, apart from the treatment of contaminated water, there exists a need more generally for a system that can separate any immiscible liquids (i.e., two or more liquids that do not form a homogeneous solution when mixed).

SUMMARY OF THE INVENTION

In accordance with the invention there is provided a system for use on an ocean vessel to process contaminated water and transmit related data to a remote facility. The invention includes a separation system, data acquisition interface, and communication unit. The separation system includes a pump and a housing that has an inlet and first and second outlets, with the pump being coupled to the housing to provide a flow of contaminated water through the housing from the inlet to the first outlet. The separation system is operable to process contaminated water flowing through the housing and supply separated contaminants to the second outlet. The data acquisition interface is coupled to the separation system and is operable to acquire data relating to processing of the contaminated water by the separation system. The communication unit is coupled to the interface to receive the data acquired by the interface. The communication unit includes an antenna and is operable to provide wireless transmission of the data to a remote facility via the antenna. Preferably, the interface can also utilize commands received by the communication system to permit remote control of the separation system. The system is particularly useful in treating and remotely monitoring ship bilge and ballast water contaminated with oil and other such hydrocarbon based liquids.

BRIEF DESCRIPTION OF THE DRAWINGS

A preferred exemplary embodiment of the present invention will hereinafter be described in conjunction with the appended drawings, wherein like designations denote like elements, and.

DESCRIPTION OF THE PREFERRED EMBODIMENT

The illustrated embodiment will be described as the invention might be used in a marine application to treat oily bilge water, ballast water, and waters from other cleaning and descaling operations. However, it will be appreciated that the invention can be used to clean any other water contaminated with hydrocarbons, reclaiming for example all oils from fuel and oil storage tanks. More generally, the invention can be used to separate any immiscible liquids, such as may be generated by manufacturing processes or machining and metalworking operations, or as may be present naturally in such things as crude oil. Moreover, while the invention is directed to separation of liquids, it can also be used to separate suspended solids from liquids where the suspended solid behave as a liquid having a different specific gravity than the liquid in which they are suspended. Accordingly, as used herein the term "liquid" will be understood to include such suspensions of solids.

OVERVIEW

Figure 1:
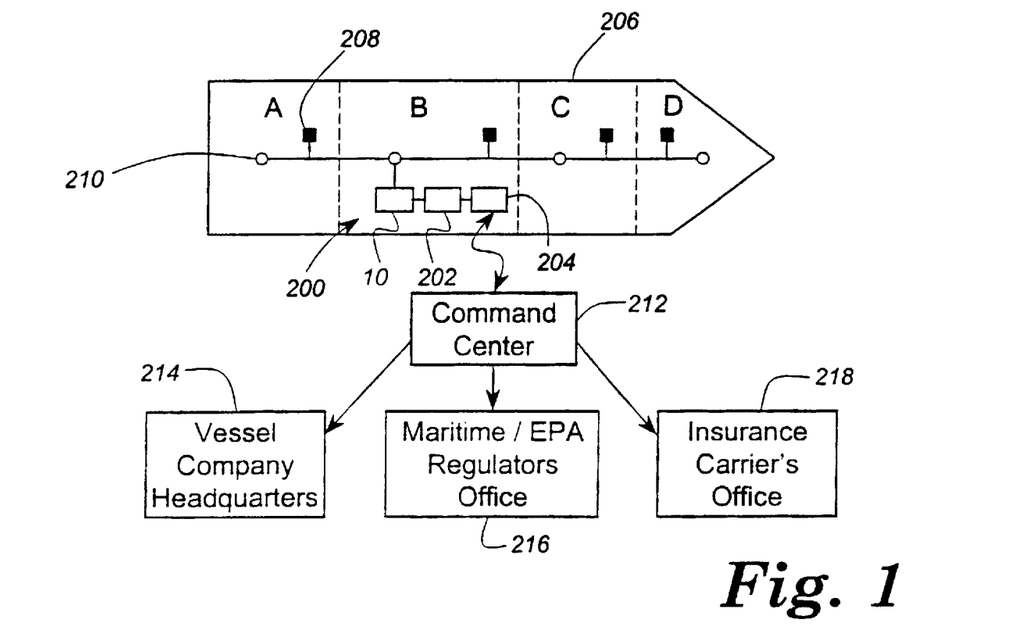
FIG. 1 is a diagrammatic view of a preferred embodiment of a shipboard system of the present invention as it would be used in conjunction with an ocean vessel to decontaminate bilge and/or ballast water.

As shown in FIG. 1, a shipboard system of the present invention, designated generally as 200, includes a separation system 10, electronic controller 202, and communication unit 204, all of which are carried on board an ocean vessel 206. The separation system 10 receives contaminated water from one or more locations A–D within the ship's bilge. Each of these locations may have its own level sensor 208 and valved pickup point 210. In general, bilge and/or ballast water from the vessel 206 is drawn from one or more of these locations A–D and are processed by separation system 10 under control of the electronic controller 202. Decontaminated water is pumped overboard while the oil and other contaminants recovered by separation system 10 are stored for later disposal or reclamation. Data relating to the processing of contaminated water by separation system 10 is sent by communication unit 204 to a remote facility, such as a command center 212, where the data or other related information can be passed on to various other facilities such as the vessel company headquarters 214, a maritime governmental or other environmental regulator 216, and the vessel's insurance carrier's offices 218. In a like manner, commands originating at the command center 212 or any the other facilities 214–218 can be transmitted back to controller 202 via communication unit 204 for remote control of separation system 10.

As will be discussed in greater detail further below, communication between the system 200 and command center 212 is preferably. by way of wireless communication and, in particular, by way of satellite communication using the INTELSAT or other suitable satellite network. Communication between command center 212 and other facilities 214–218 can be by any suitable means, such as via land lines. During normal operation of separation system 10, data relating to the operation of the system is continuously monitored by the controller 202 and can be periodically reported back to command center 212. The reported data can be passed on to the other facilities 214–218, thereby permitting real-time monitoring.

This remote monitoring can be utilized by the vessel corporate headquarters 214 to detect leaks or excessive contaminations from the various vessel mechanical and fluid systems. For example, oil contamination in section A may be generated from hydraulic rudder systems, stem thrusters, the propeller shaft, or other mechanical process equipment. Upon determining that an excessive amount of oil exists, controller 202 can send an alert to the command center 212 as well as to the ship's onboard engineer for immediate investigation. The monitored data can also be used to determine and update maintenance schedules for the vessel equipment. This monitoring can be used by the maritime regulator 216 and insurance carrier 218 to monitor compliance with governmental regulations and other pre-established criteria.

CONSTRUCTION OF THE SEPARATION SYSTEM

Figure 2:
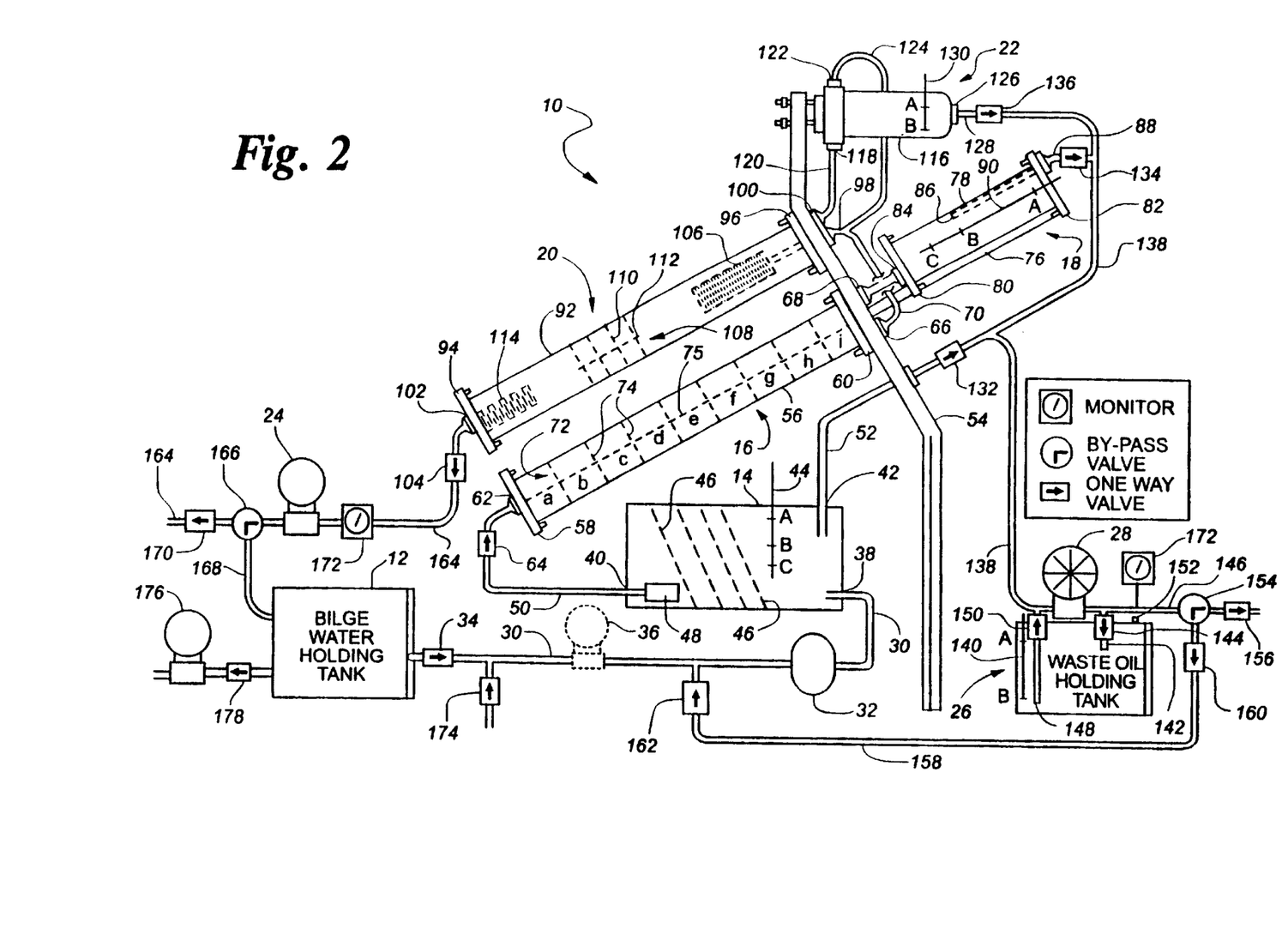
FIG. 2 is a side view and partially schematic view of the oil/water separation system of FIG. 1.

Referring now to FIG. 2, there is shown separation system 10 which includes as its main components a bilge water holding tank 12, pre-filter tank 14, separator 16, oil accumulator 18, coalescer 20, air refining chamber 22, pump 24, waste oil holding tank 26, and a second pump 28. In general, oily or otherwise contaminated bilge water is drawn by pump 24 from holding tank 12 and is then processed sequentially through pre-filter tank 14, separator 16, and coalescer 20 and can thereafter be pumped overboard after any further treatment if needed. At each stage in the process, oil is separated out from the water and accumulates at the surface of the water in pre-filter tank 14, oil accumulator 18, and refining chamber 22. Using pump 28, the accumulated oil can be intermittently or continuously pumped from these vessels into waste oil holding tank 26.

Bilge water holding tank 12 is connected via an intake line 30 to a coarse strainer 32 and then to pre-filter tank 14. Strainer 32 prevents debris such as sea weed from entering pre-filter tank 14 and can comprise a wire mesh or plates with 1.8" perforations. A one way valve 34 is connected in series with intake line 30 to permit control over the supply of bilge water to the system and to prevent any backflow from the system into holding tank 12. If desired, an optional pump 36 can be placed in series with intake line 30 to fill pre-filter tank 14. Pump 36 may be needed if the suction from pump 24 is insufficient to draw the contaminated water from holding tank 12 into pre-filter tank 14.

Pre-filter tank 14 includes an inlet 38, water outlet 40, oil outlet 42, level sensor 44, filter plates 46, and a grit filter 48. Intake line 30 opens into pre-filter tank 14 at its inlet 38. Connected to water outlet 40 is a separator feed line 50. Grit filter 48 is located at the inlet of feed line 50 and is used to prevent dirt and grit from entering separator 16. Preferably, grit filter 48 filters the contaminated water leaving tank 14 down to approximately 150 microns. Oil outlet 42 is located at the top of tank 14 and is connected to an oil waste line 52 through which the separated oil can be transferred to waste oil holding tank 26. Level sensor 44 can be a dual bulb sensor as will be known to those skilled in the art. Level sensor 44 senses the level of oil and water in tank 14 at levels A, B, and C and is used in priming the system and to insure that proper levels in tank 14 are maintained during operation. Filter plates 46 are inclined, perforated plates that operate to create a laminar flow across tank 14 from its inlet 38 to its outlet 40. This arrangement has been found to operate more efficiently than traditional inclined plate separators and weir separators.

Figure 3:
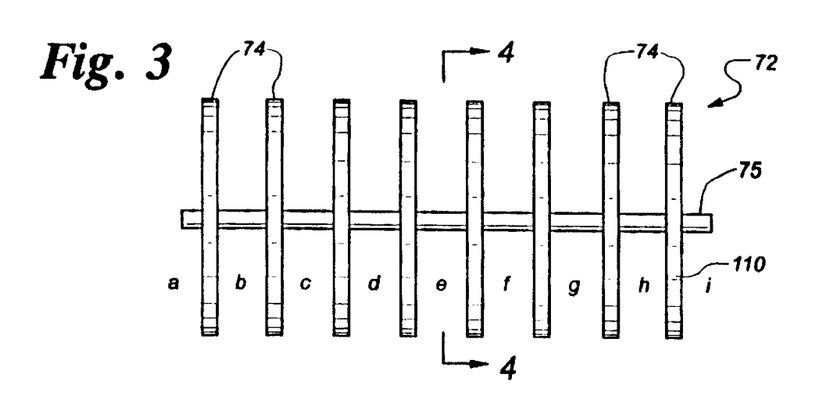
FIG. 3 depicts a side view of the separator plate assembly used within the separation system of FIG. 2.
Figure 4:
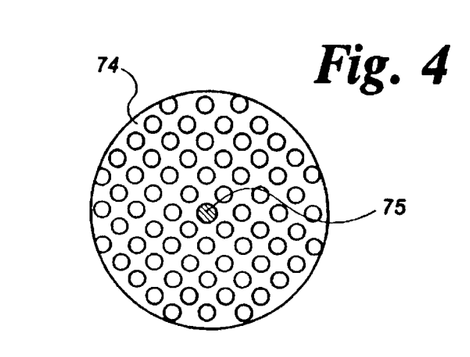
FIG. 4 is a sectional view taken along the 4—4 line of FIG. 3 showing a side view of the perforated plates used in the separator plate assembly of FIG. 3.

Separator 16 is supported on a frame 54 and comprises a cylindrical housing 56 that extends from a lower end 58 to an upper end 60. Separator 16 includes an inlet 62 at its lower end 58 which is connected via a one-way valve 64 and feed line 50 to the outlet 40 of pre-filter tank 14. At the upper end 60 of housing 56 is a water outlet 66 and an oil outlet 68. Water outlet 66 is connected via a coalescer feed line 70 to coalescer 20. Oil outlet 68 is connected directly to oil accumulator 18 which is located above the upper end 60 of housing 56. Located within separator 16 is a separator plate assembly 72 that comprises a number of spaced plates 74. These plates divide separator 16 into a plurality of sequential chambers, as indicated in FIG. 2 by the letters a–i. Referring briefly to FIGS. 3 and 4, separator plate assembly 72 comprises a number of polypropylene plates 74 and a center retaining rod 75. Plates 74 are perforated with 3/16" holes on 7/16" centers and the plates are spaced approximately 3–4" apart. The open cross-sectional area of the plates is approximately 30–33% of the total cross-sectional area. The diameter of the perforated plates is within ten thousands of an inch of the internal diameter of housing 56 so that the plates fit snugly into housing 56 and will only permit negligible water flow between the plates and housing 56. Retaining rod 75 extends through each of the plates 74 and attaches to housing 56 at its upper end 60. The oil is attracted to the polypropylene plates which helps separate the oil from the water flowing past the plates. Also, the plates act as flow restrictors that prevent channeling of water or oil as it traverses housing 56 and that provide a laminar flow of the water and oil through each of the chambers. This aids in the separation of oil and water.

Oil accumulator 18 is supported on an extension 76 of frame 54 and comprises a cylindrical housing 78 that extends from a lower end 80 to an upper end 82. Accumulator 18 has an oil inlet 84 at its lower end 80 that is connected to outlet 68 of separator 16. Accumulator 18 is located on frame 54 above separator 16 so that the oil from separator 16 will flow upwards into accumulator 18 displacing the water held therein. At the upper end 82 of accumulator 18 is an oil outlet 86 that is connected to an oil waste line 88 that permits oil within accumulator 18 to be transferred to waste oil holding tank 26. Accumulator 18 includes a level sensor 90 that can be the same as or similar to level sensor 44 and that is used in priming the system and to determine that the proper levels are maintained in accumulator 18 during operation.

Figure 5:
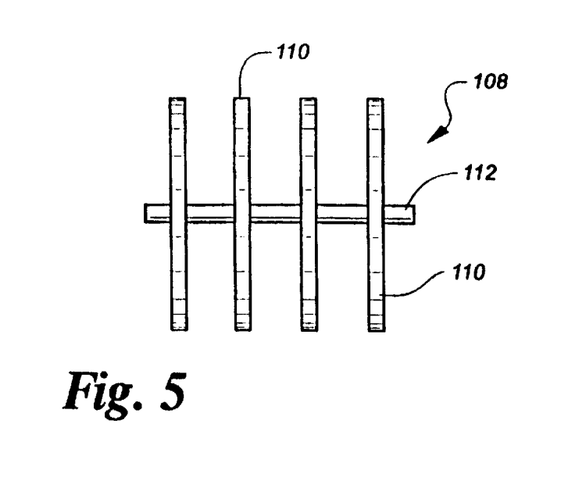
FIG. 5 depicts a side view of the coalescer plate assembly used within the separation system of FIG. 2.

Coalescer 20 is supported on frame 54 next to separator 16. Coalescer 20 comprises a cylindrical housing 92 extending between a lower end 94 and an upper end 96. Coalescer 20 includes an inlet 98 and oil outlet 100 at its upper end 96. Inlet 98 is connected to feed line 70 to receive water from separator 16 and outlet 100 is located above inlet 98 and is connected to air refining chamber 22. At lower end 94 of housing 92 is a water outlet 102 that is coupled via a one-way valve 104 to pump 24. Coalescer 20 includes an air scrubber 106 that is used to inject the water received at inlet 98 into the interior of housing 92 along with air bubbles that provide a cross-flow air scrubbing of the water as it travels from air scrubber 106 down towards water outlet 102. Coalescer 20 also includes a coalescer plate assembly 108. Referring briefly to FIG. 5, plate assembly 108 comprises a number of polypropylene plates 110 that are identical to plates 74 of separator 16. A center retaining rod 112 extends between each of the plates 110 to maintain their spacing. The plates are spaced approximately four inches apart. Coalescer 20 also includes a well suction screen or well point 114 having slits that are 1/64" in width and spaced 3/16" apart. Well point 114 helps maintain a laminar flow at the water outlet 102 of coalescer 20.

Air refining chamber 22 is an air/oil accumulator that receives and retains the oil removed in coalescer 20. Chamber 22 comprises a vessel 116 that is mounted on frame 54 above coalescer 20. It includes an air/oil inlet 118 on its underside that is connected to oil outlet 100 of coalescer 20 by a substantially vertically-extending feed line 120. At the top side of refining chamber 22 is an air outlet 122 that is connected back to coalescer feed line 70 via an air return line 124. At one end of chamber 22 is an oil outlet 126 that is connected to an oil waste line 128. Refining chamber 22 includes a level sensor 128 that can be the same as or similar to that used in pre-filter tank 14, except that only two levels A and B need be detected by the sensor.

As mentioned above, oil that has accumulated in either pre-filter tank 14, oil accumulator 18, or refining chamber 22 is periodically or continuously transferred to waste oil holding tank 26 using pump 28. This is accomplished using one-way valves 132, 134, and 136 that each feed into a common oil waste line 138 that is connected to pump 28. These valves allow oil to be drawn from tank 14, accumulator 18, and chamber 22 independently of each other.

Waste oil holding tank 26 includes a level sensor 140 that can be a dual bulb sensor as used for the other level sensors of separation system 10. Holding tank 26 has a waste oil inlet 142 that is connected via a one-way valve 144 to discharge line 146 at the pressure side of pump 28. Holding tank 26 also has a waste oil outlet line 148 that extends from the bottom of tank 26 through a one-way valve 150 to the vacuum side of pump 28. Holding tank 26 can be an industrial drum or other closed vessel in which case it includes a vent 152 to permit airflow into and out of the tank when oil is added or removed. In series with discharge line 146 is a bypass valve 154 and one-way valve 156. Bypass valve 154 is connected via a return line 158 back to intake line 30 so that liquid held in tank 26 or drawn from pre-filter tank 14, oil accumulator 18, or refining chamber 22 can be returned to pre-filter tank 14 for further processing. One-way valves 160 and 162 at each end of return line 158 are used along with bypass valve 154 to control the flow of liquid back to intake 30 when desired.

As mentioned above, the outlet 102 of coalescer 20 is coupled to pump 24 via a one-way valve 104. This is accomplished using a clean water discharge line 164. A bypass valve 166 is located in series with water discharge line 164 and is connected to a return line 168 so that water can be returned to bilge water holding tank 12 for further processing. A final one-way valve 170 can be located in discharge line 164 past valve 166 to control the dischage of water. To monitor operation of the system, monitors 172 such as vacuum gauges, pressure gauges, or flow meters can be placed at various points in the system. For addition of clean water (such as fresh seawater), a one-way valve 174 can be connected between a source of clean water and intake line 30. Also, separation system 10 can include an emergency bilge pump 176 and one-way valve 178 to discharge the contents of holding tank 12 if necessary.

As shown, separator 16, oil accumulator 18, and coalescer 20 are inclined so that the oil will move upwards into accumulator 18 and refining chamber 20, replacing water held therein. Chamber 22 is shown in a generally horizontal orientation, but can be inclined as well with air outlet 120 being located at the uppermost part of the vessel. Preferably, separator 16, oil accumulator 18, and coalescer 20 are inclined at an angle relative to horizontal within the range of 22–45° and, even more preferably, is set at an angle of approximately 22°.

Figures 6, 9:
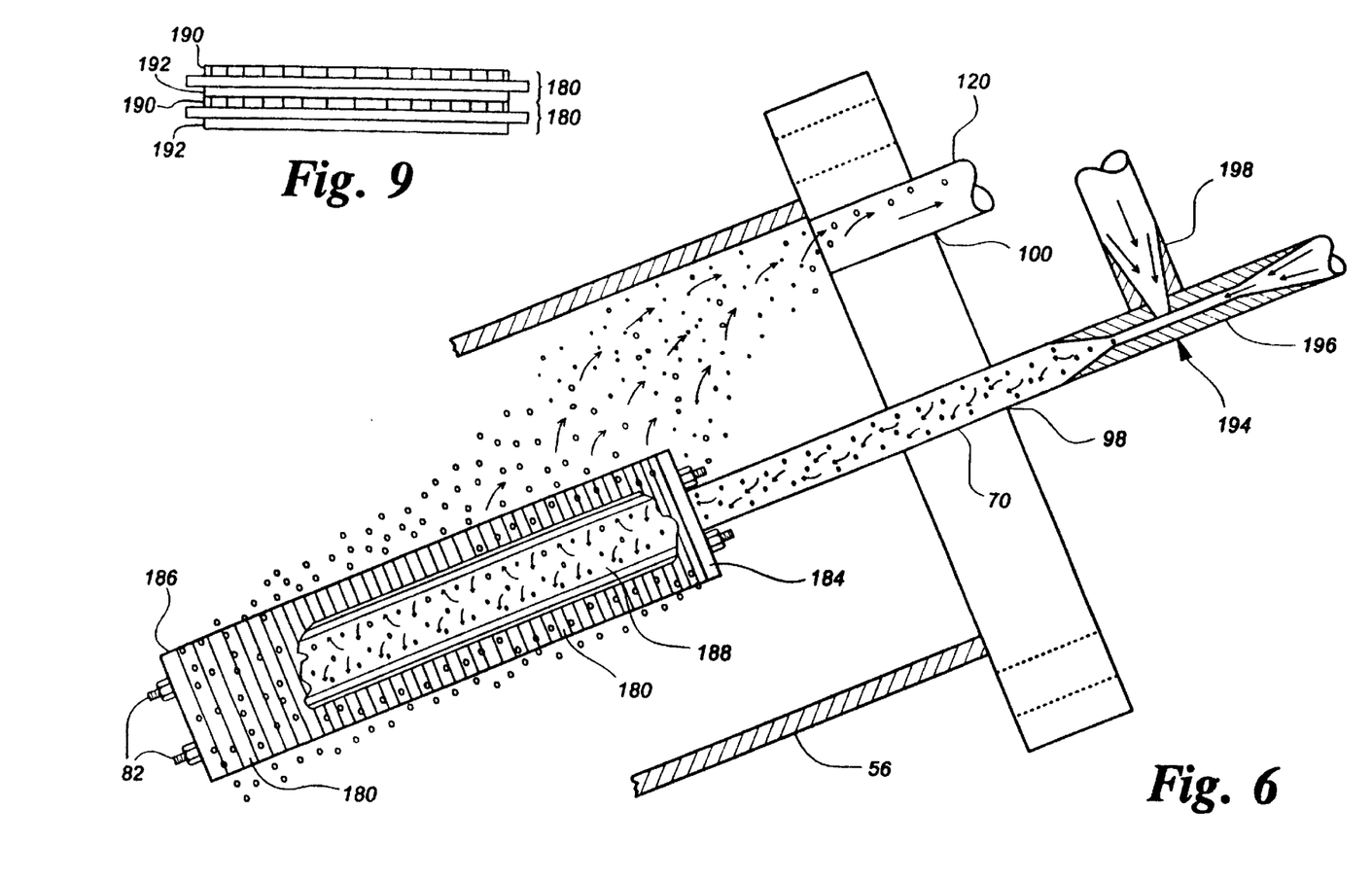
FIG. 6 is an enlarged fragmentary view of a portion of the separation system of FIG. 2 showing the air scrubber located in the upper portion of the coalescer.
FIG. 9 is a side view showing two of the annular plates of FIGS. 7 and 8 stacked together.

Turning now to FIG. 6, air scrubber 106 is shown further detail. Air scrubber 106 is made up from a series of wafer-thin annular disks 180 of polypropylene. The disks are held stacked together with three retaining rods 182 (only two shown) that clamp the disks between two solid end caps 184, 186. Together the disks 180 and end caps 184, 186 define an inner chamber 188 into which air and water flow from coalescer feed line 70. The end caps are approximately ¼" in diameter larger than the polypropylene disks 180 and the top end cap 184 has a ¾" threaded hole through which feed line 70 passes. The disks 180 are approximately ⅛" thick with air scrubber 106 utilizing approximately 100 disks for a total length of twelve inches. The disks have oppositely oriented ridges on each side which, when stacked and held together with the retaining rods 44, make up the specific pore sizes for air scrubber 106. Different pore sizes may be required for different oils.

Figure 7:
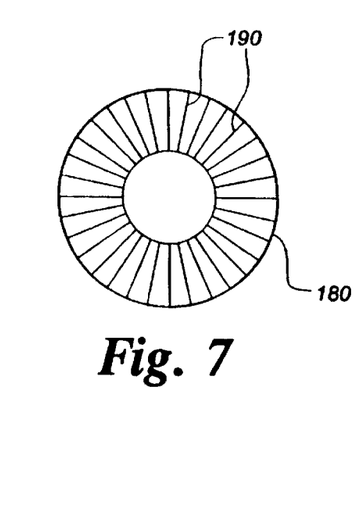
FIG. 7 is top view of one of annular plates shown in FIG. 6.
Figure 8:
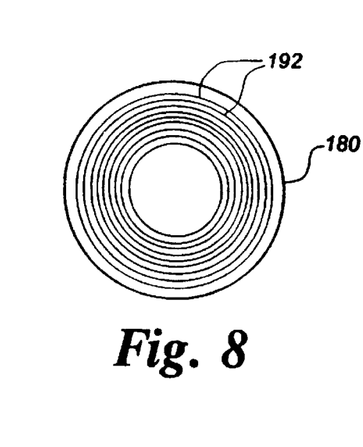
FIG. 8 is a bottom view of the annular plate of FIG. 7.

Referring momentarily to FIGS. 7–9, the construction and arrangement of the polypropylene disks 180 will now be described. The disks can each have an outer diameter of two inches. One side of each disk 180 has radially-extending ribs 190, as shown in FIG. 7. The other side of each disk has a series of concentric ribs 192, as shown in FIG. 8. Thus, as depicted in FIG. 9, when two disks 180 are stacked together the concentric ribs 192 overlie the radial ribs 190, thereby creating a sinuous path between inner chamber 188 and the exterior of air scrubber 106. Water entering inner chamber 188 flows outwardly across the surface of the disks, traveling along the sinuous path between the ribs 190 and 192. The polypropylene attracts the oil which coalesces to form larger droplets that then float upwardly, exiting coalescer 20 through air/oil outlet 100. The disks can be the same as that used in the Ein-Tal 30 mesh water filter, part number 06-21-30.1 available from Homeland Irrigation of Vero Beach, Fla. As will be appreciated, materials other than polypropylene can be used, such as polyethylene or even stainless steel depending upon the application. As an alternative design to that depicted in the illustrated embodiment, each disk can be designed to include a circular set of intermittent serpentine ribs and a series of concentric circular intermittent ribs on each side. The ribs can be ¹⁄₃₂" in height and width. The serpentine ribs on the top side of the disk would be located at a slightly different radial distance than the serpentine ribs on the bottom of the disk so that, when the disks are stacked together, the top side serpentine ribs of one disk interlock with the bottom side serpentine ribs of the next disk to maintain a ¹⁄₃₂" space between the adjacent ends of the raised ribs when the disks are assembled. Furthermore, the height of the ribs and the amount of spacing between the ends of adjoining ribs can be adjusted depending upon the type and amount of oil to be separated out.

Referring back to FIG. 6, air from refining chamber 22 is injected via air return line 124 into the water entering coalescer 20 through feed line 70. This is accomplished using an air injection manifold 194 connected in-line with feed line 70. Injection manifold 194 includes a restriction 196 and a venturi inlet port 198 that is located in restriction 196 and that is connected to the top of refining chamber 22 via air return line 124. As will be understood by those skilled in the art, water flowing through injection manifold 194 will accelerate to a higher velocity as it moves through restriction 196, creating a venturi effect at inlet port 198. This vacuum pulls air from refining chamber 22 which is drawn into the water flowing through manifold 194. This air then enters air scrubber 106 where oil attaches to it while it bubbles out and carries the oil up into refining chamber 22.

OPERATION OF THE SEPARATION SYSTEM

Figure 10:
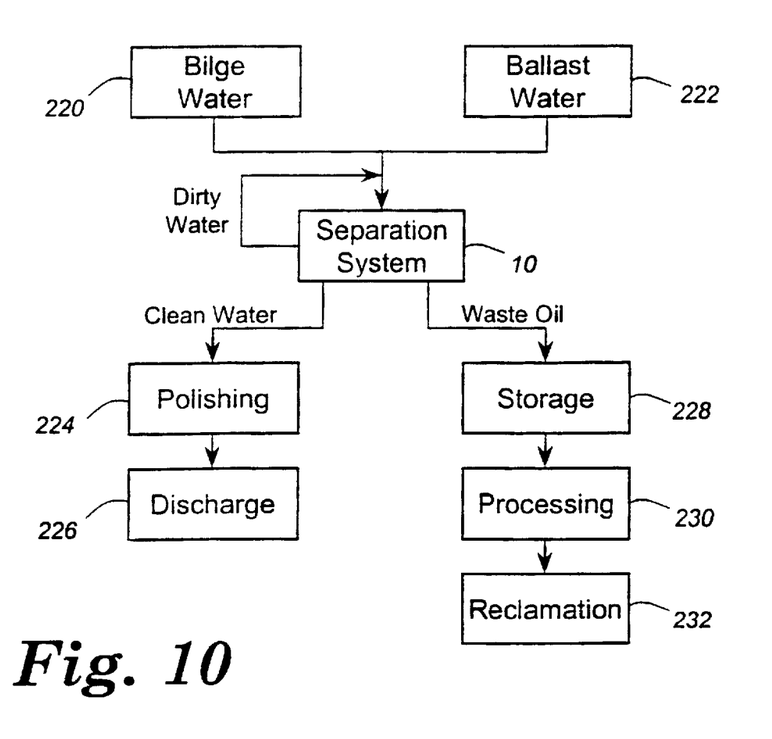
FIG. 10 is a process flow overview showing how the separation system of FIG. 2 can be used to process contaminated bilge and ballast water.

Turning now to FIG. 10, the normal use and operation of separation system 10 will now be described. Separation system 10 itself operates in sequential stages, removing finer and finer droplets of the oil at each stage. Unlike conventional systems that use fine filtration elements to separate the smaller droplets of oil, separation system 10 operates to convert these droplets into larger droplets that are easily separated from the water. The remaining water is treated by a cross flow air scrubbing to remove residual oil and other hydrocarbons.

As shown, water from the bilge 220 and ballast tanks 222, if present, are pumped or otherwise drawn into separation system 10 for decontamination. Depending upon the level of contamination, a portion or all of the dirty water may be recirculated. Clean water removed from the separation system 10 can be put through one or more polishing steps 224 prior to being discharged 226. Waste oil separated out by the system is held in a storage tank 228 for later disposal or reclamation. If desired, the system can also include additional processing equipment 230 for onboard recovery or reclamation 232.

With reference back to FIG. 2, the system must initially be primed to charge the system with water and to establish the proper levels for efficient operation of the system. Fresh seawater may be used for this purpose. The first step in the priming operation is to open clean water valve 174, pre-filter waste line valve 132, and the waste oil holding tank inlet valve 144. All other valves are closed at this point. Then, pump 28 is started to draw fresh water through intake line 30 and into pre-filter tank 14. If needed, optional pump 36 can be used to pull clean water through intake line 30 and into tank 14. The clean water is added to tank 14, until level A on sensor 44 is reached. Then, valve 132 is closed while separator inlet valve 64 and oil accumulator outlet valve 134 are opened. The clean water is drawn into separator 16 and oil accumulator 18 until the high level A on sensor 90 is reached. Then, valve 134 is closed and refining chamber oil outlet valve 136 is opened. This results in coalescer 20 being filled with clean water followed by refining chamber 22 being filled. Once the high level A of sensor 130 is reached, valves 136 and 144 are closed and pump 28 is turned off. The system is now primed.

Normal operation begins by starting pump 24 and opening bilge water inlet valve 34 and cleaned water discharge valve 170. Pump 24 draws water from coalescer 20 and, within one minute establishes a system vacuum of about two to three inches of Mercury (Hg) through coalescer 20, separator 16, and pre-filter tank 14. By operating under vacuum, the line velocity of the fluid is slower than in most pressurized systems, thereby reducing the mechanical emulsification of oils. The reduced turbulence provided by this vacuum draw helps permit separation of the oil from the water. Since waste line valves 134 and 136 are closed, no water is drawn out of oil accumulator 18 or refining chamber 22 even though they experience the system vacuum pressure. After passing through strainer 32, the contaminated bilge water enters pre-filter tank 14 where the initial separation of oil and water occurs. Approximately 95% of the oil accumulates within tank 14. In addition to this initial separation, tank 14 operates to balance the flow from bilge water holding tank 12.

The water then moves to separator 16 after first passing through grit filter 48 which removes any dirt or other solid particles. Separator 16 provides a laminar flow to help settle out oil and utilizes the polypropylene perforated plates 74 to accumulate small droplets of oil and control the flow of water through the separator. Initially, the water enters chamber a of separator 16 in a turbulent manner. As the water moves across the first plate from chamber a to chamber b, the turbulence is reduced and the oil starts to rise to the top of the chambers. As the water moves through the chambers, more oil rises to the upper portion of each chamber. It has been found that the majority of the oil separates in the first five chambers and that only a small portion of the remaining oil separates in the last four chambers. The oil flows upward from chamber to chamber at the very top portion of each chamber until it reaches upper end 60. At this point the oil moves up into oil accumulator 18, displacing the water held therein which flows down into separator 16.

The water is then drawn into coalescer 20 via air scrubber 106. At this point, the water is substantially clean except for the finer droplets of oil and oil having a relatively neutral buoyancy. Coalescer 20 allows the finer oil droplets to combine into larger droplets that move up into air refining chamber 22 where they displace water that moves down into coalescer 20. Also, the air bubbles leaving air scrubber 106 accumulate light oils and fine oil droplets on their surface. These are carried upwards with the air bubbles into chamber 22. The perforated polypropylene plates 110 within coalescer 20 provide a final opportunity to accumulate oil by forming larger droplets that then float up into chamber 22. At this point, the water is essentially oil free and it leaves coalescer 20 via well point 114 which works to prevent the occurrence of a vortex as the fluid exits through outlet 102. The cleaned water can then be discharged into the ocean.

Bilge water inlet valve is kept open as long as the level within pre-filter tank 14 stays below A on level sensor 44. As the system continues, more and more of the water within tank 14 is replaced by oil. Once the oil level reaches down to level B on sensor 44, pump 28 is started and waste line valves 132 and 144 are opened to transfer the oil into holding tank 26. Similarly, once enough oil has replaced the water in oil accumulator 18 and refining chamber 22 such that the oil reaches B on their respective level sensors, pump 28 is started while tank inlet valve 144 and either waste line valve 134 or 136, or both, are opened to transfer the oil to holding tank 26. Once the oil level in holding tank 26 reaches level A on its sensor, pump 28 is started while holding tank outlet valve 150 and waste discharge valve 156 are opened. The reclaimed oil discharged through valve 156 can be pumped into drums for transporting to a suitable processing facility.

Depending upon the application and level of decontamination needed, additional separators and/or coalescers can be added, either in series for improved decontamination or in parallel for higher system flow rates. Also, optional processing of the clean water exiting separation system 10 can be carried out. This can include micro filtration and particle filtration down to, for example, 5 microns, organic filtering to remove dissolved hydrocarbons, ionic filtration for absorption of dissolved metals, and ultra filtration by reverse osmosis. Other such polishing steps will be apparent to those skilled in the art.

CONSTRUCTION OF THE CONTROLLER AND COMMUNICATION SYSTEM

Referring again to FIG. 1, controller 202 at a minimum comprises a data acquisition interface that is coupled to separation system 10 to acquire data relating to processing of the contaminated water by the separation system. The controller is a microprocessor-based circuit that is operable under program control to transmit the data to the communication unit 204 for satellite transmission to the command center 212. Controller 202 can monitor data relating to operation of separation system 10 using any of the meters or other sensors discussed in connection with FIG. 2. Thus, controller 202 can be used to monitor flow rates at various locations within separator system 10, as well as fluid levels within the various tanks and accumulators. Temperature sensors, pressure sensors, water level sensors, and other such sensors, whether included as a part of separation system 10 or located other places within the ship 206, can also be connected to controller 202 for monitoring purposes. Furthermore, controller 202 preferably includes one or more outputs coupled to various ones of the pumps, valves, or other control elements of separation system 10. This permits remote control of the operation of the system.

For purposes of data acquisition, controller 202 includes an analog to digital converter (not shown) which digitizes the signals received from the various sensors. The digital data is then provided to the microprocessor for storage in onboard memory, transmission to the communication unit 204, and, if desired, trending and other analysis onboard by the microprocessor. The design and programming of this controller circuitry is well within the knowledge of those skilled in the art and will therefore not be further elaborated upon here.

When necessary, the programming used by controller 202 may either be updated via the satellite link or when the ship is in port. Preferably, controller 202 includes a touch screen that displays a graphical user interface that permits setup of the monitored parameters as well as setup of trending analysis and alarm limits. Controller 202 can also have suitable programming for the purpose of onboard training of new operators for the system. Operational manuals, troubleshooting guides, operator documentation, and training materials can all be made available on screen. Furthermore, controller 202 can be password protected to provide system security so that only properly trained and authorized people will be able to actually operate or change the system settings.

The data acquired by controller 202 can be monitored for a variety of purposes, including leak detection and compliance with governmental regulations. Monitoring of the data for purposes of leak detection permits the system to be used proactively in an effort to identify and address mechanical problems before the occurrence of a catastrophic event. The system can monitor the quantity of liquids that have entered the bilge, the amount of decontaminated water pumped from the system, as well as the amount of oils or other immiscible liquids that have been removed from the contaminated water. As mentioned above, these oils and other liquids may be the result of spills or leaks from various mechanical or fluid systems on the vessel. Once initial data baselines have been established, the volume of oil removed on a daily basis can be trended and monitored and this data used to determine if an excessive amount of oil begins to appear in the bilge water, possibly indicating a leak or spill that requires the ship engineer's attention. Similarly, by managing the ballast waters through the system, the integrity between the ballast tanks and other holding tanks and areas of the vessel can be monitored. In this way, leaks in the bilge and/or ballast tanks can be identified, repaired, and resolved prior to further ship deterioration and environmental risk.

The detection of leaks or other abnormal operating conditions can be determined using alarm limits. Controller 202 monitors data from the various sensors on separation system 10 and, upon detecting that he measured parameter of the system operation crosses an alarm limit, generates an alert that is sent both to the ship's engineer and to the command center 212. As long as the system is operating within parameters, the data can just be accumulated by controller 202. In the event that the controller 202 detects a parameter that exceeds its alarm limit or that displays a certain amount of spikes within a specified time period, an alert will be sent to the command center to evaluate whether any of the operational parameters need to be changed or whether the condition is of the type does not critical and will not likely repeat in the future. The controller can also monitor and generate an alarm in the event of high volumes of water coming into a chamber where the system is processing more water than has been typically established for a time period, whether over the course of hours, days, or weeks.

The shipboard system 200 includes a global positioning system (not shown) that permits controller 202 to determine and report the global position of the vessel at any one time. This global positioning information can be used for a variety of purposes. For example, in the event that the operation of the separation system 10 is bypassed and bilge or ballast water is discharged overboard, controller 202 can send an alert to the command center 212 along with the ship's current position. This information can be used by governmental regulators to determine whether the discharge was within protected waters. Also, by being able to monitor such information, the vessel company may be able to demonstrate to regulators and its insurers a reduced risk of environmental impact, thereby enabling the vessel company to qualify for reduced insurance premiums. For military and other government operations involving circumstances in which it is not desirable to transmit the ship's global position, the global position data can be accumulated on board and manually downloaded at a later time when the ship is in port.

Where the ship includes a bypass device (that is, a bypass valve and/or pump), the controller can include coastal mappings or other position data that identifies environmentally regulated or otherwise protected waters to thereby prevent the discharge of contaminated water when the ship is located in the protected waters. In particular, the controller 202 can use the position data along with the ship's global position (as reported by the global positioning system) to permit operation of the bypass device when the vessel is in unregulated waters and to inhibit operation of the bypass device when the vessel is in the protected waters.

The controller 202 can also use the position data to automatically control the discharge of bilge and/or ballast water when the ship enters shallow waters. For example, the controller 202 can store depth data along with the position data so that, as the ship comes into port, the controller can determine the current draft of the ship, as well as the required draft for that particular port and, if necessary, can reduce the ship's draft by discharging water overboard. This determination could be done in conjunction with other conditions and variables, including sea state, total bilge or ballast water volumes, and ship speed, as will be appreciated by those skilled in the art.

Although a single separation system 10 is shown in FIG. 1 as it would be utilized in treating contaminated water from various sections of the vessel 206, it will be appreciated that each location A–D can have its own separation system 10, each of which can be operated by a single controller 202. Reporting of data back to the command center 212 would therefore involve multiplexing of the data from each of the separation systems 10, with each separation system 10 being uniquely identified by the controller 202 so that the reported data could be correlated with the proper location on the vessel 206.

Figures 11, 12:
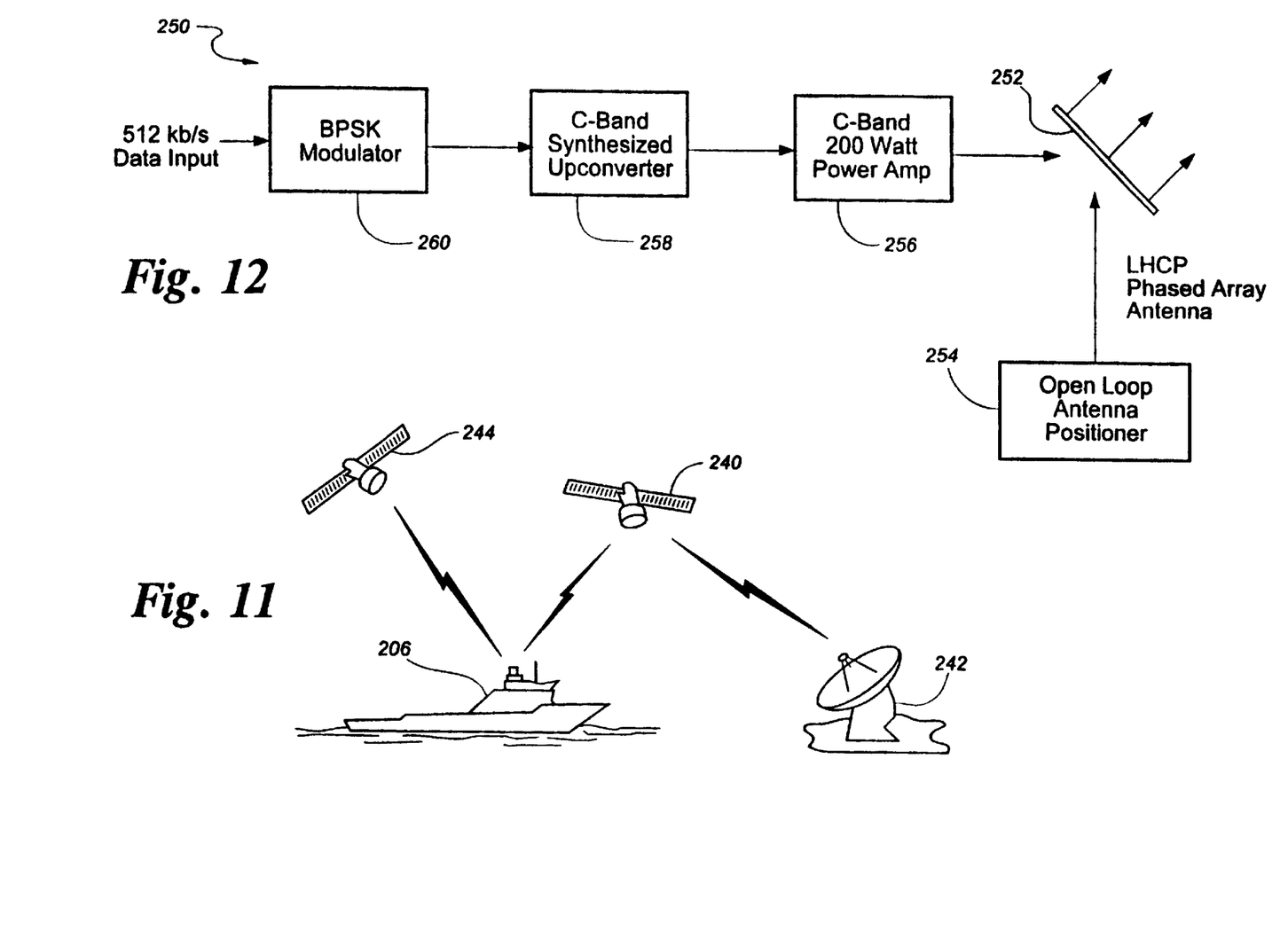
FIG. 11 is a diagrammatic view of the satellite communication link used with the system of FIG. 1 to exchange data and commands between the system and a remote facility.
FIG. 12 is a block diagram of a communication unit used as a part of the system of FIG. 1 to communicate with the remote facility via the communication link of FIG. 11.

As mentioned above, communication between the system 200 and the command center 212 is preferably by way of satellite. This is shown in FIG. 11. The communication link associated with system 200 serves two distinct purposes; one for forwarding data (ship to shore) and the other for controlling the system 200 and/or other shipboard hardware components (not shown) from shore. The communication link provides both a high data rate link and a monitor and control (M&C) link. The high data rate link is a 512 kb/s simplex circuit from a shipboard SATCOM terminal (not shown) that comprises a part of the communication unit 204 shown in FIG. 1. The SATCOM terminal can be used to provide this high data rate link via an INTELSAT satellite 240 to a mainland Standard-A earth station 242 that can be located at the command center 212 or in communication therewith via land lines or another wireless communication path. This link can be used to transfer all or a portion of the data monitored by controller 202, as well as shipboard satellite terminal status messages that are multiplexed into the data stream. The data transfer is near real time with less than 1 second delay as seen by the end user. The low bit error rate (BER<$10^{-8}$) can be achieved by using a Forward Error Correcting (FEC) coding algorithm consisting of a convolutional code concatenated with a Reed-Solution block code. After data is received at the command center 212, it is then delivered to one or all of the other facilities 214–218 either by dialup or dedicated terrestrial TELCO services. Alternatively, data can be saved at the command center 212 as files and accessed by the other facilities via the Internet.

Control of the system 200 from shore (the M&C link) can be accomplished using INMARSAT-C 600 b/s store and forward data transfer service. The remote control link is generally a one-way link to the ship 206 via an INMARSAT-C satellite 244 for control of sensors and various shipboard components, such as the separation system's valves, pumps, and other control elements. However, this link is also capable of returning hardware status messages from the ship as a backup to the primary high data rate path. Data transfer from the INMARSAT coastal station (not shown) can be done in any of a variety of manners, including via Internet e-mail. For dedicated service, the INMARSAT-C can also be provided directly to the user or designated regulatory agencies.

To achieve the high data rate transfer, communication unit 204 also includes a very small aperture terminal (VSAT), available from Harris Corporation's Maritime Communication Services (MCS). As shown in FIG. 12, the VSAT 250 comprises a 32"-diameter, 36 element C-band phased array antenna 252, a three-axis antenna positioner 254 (housed in a protective radome) and a 200 watt power amplifier 256 with a frequency upconverter 258, and a Bi-Phase Shift Key (BPSK) modulator 260. Multiplexed serial data is input to the BPSK modulator 260. The Intermediate Frequency output of the modulator 260 is connected via coax to the synthesized C-band upconverter 258 capable of tuning the 5850 to 6425 MHz frequency band in 125 kHz increments. The 200 watt power amplifier 256 boosts the frequency converted signal to the desired level for transmission over the satellite 240. The amplifier's output is connected via low-loss waveguide to the input of the left hand circularly polarized phased array antenna 252 in the radome.

The system is unique in that it employs a fixed beam, mechanically steered phased array antenna designed to minimize size and weight thus allowing for minimum pointing error in this highly dynamic environment. Due to the high dynamics of an ocean-based platform, a small aperture (broad beam) and lightweight antenna is required to maintain pointing accuracy and EIRP stability in the direction of the satellite. The small size and lightweight of the phased array allows the antenna positioning system to respond quickly to ship dynamics providing increased pointing accuracy.

The tracking system uses a program track algorithm derived from either the INTELSAT 11 element set or NORAD-2 line set and combines this data with an on-board attitude and heading reference system to establish the correct "look angle" at all times. The service leases a portion of an INTELSAT satellite transponder to support the high-speed data service.

OPERATION OF THE CONTROLLER AND COMMUNICATION SYSTEM

Figure 13:
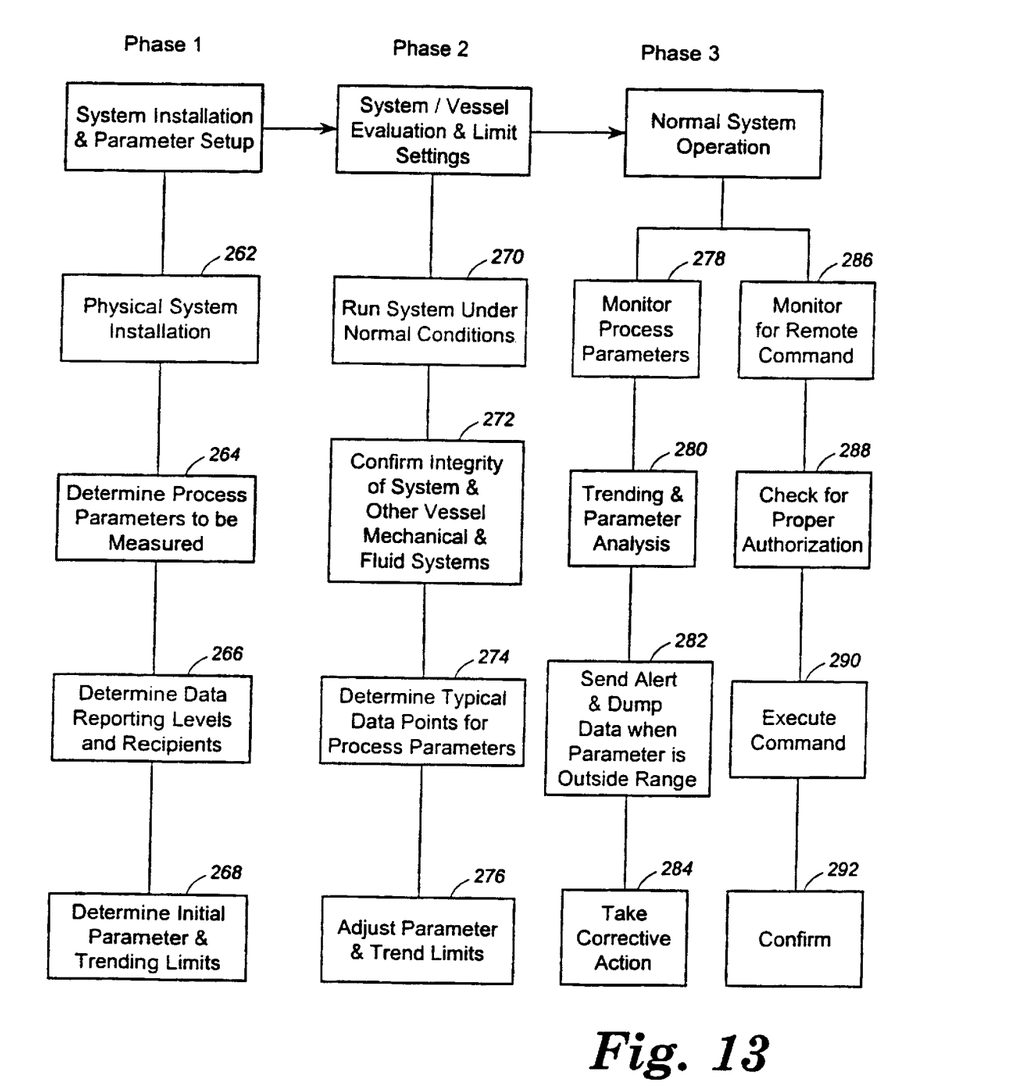
FIG. 13 is a flow chart depicting a three-phase approach to set up and operation of the system of FIG. 1.

Referring now to FIG. 13, the system installation and implementation is preferably carried out in three phases. The first phase is the system installation and parameter setup, as represented by blocks 262–268. The second phase involves system and vessel evaluation and alarm limit settings, as represented by blocks 270–276. The third phase constitutes the normal system operation, as represented by blocks 280–292.

Phase 1 is the installation mode which is used for the physical installation of the system and software configuration. Initially, the system is physically installed and primed, as described in greater detail above. Then, the software is configured to identify the different process parameters (e.g., oil and water levels, system flow rates, temperatures, pressures, etc.) that are to be monitored by the controller. Next, the software is configured to specify the data reporting levels and recipients; that is, what data is reported and to whom. This may involve specifying that all data is to be sent in real time, that the data is to be accumulated and only sent periodically, or perhaps that only summary information and averages are to be reported back to the command center. Finally, initial alarm limits and trending alarm limits are set for the various monitored parameters. These alarm limits can be initially established based upon the oil and fluid capacities of the various systems located within the ship. Where different sections (A–D) of the ship are processed by the system independently of the other sections, separate alarm limits can be established for each section.

For any one parameter, different sets of alarm limits can be utilized. For example, one set of alarm limits can be used based upon the amount of oil recovered over a 24-hour period (to thereby permit quick detection of high-volume leaks), whereas another set of alarm limits can be used based upon the amount of oil recovered over a one-week period (to thereby monitor for slower, but significant leaks). Also, alarm limits can be set based upon the rate of increase of the amount of oil recovered. Other such variations will become apparent to those skilled in the art.

Phase 2 is an evaluation mode which is used to establish the typical operating ranges (baselines) and narrow the alarm limit ranges based upon empirical data obtained from actual operation of the system. This phase involves operating the system under normal conditions and evaluating the oil accumulation rate and discharge volume rate as well as other system parameters to confirm that there are no leaks or other unusual conditions that would affect the baseline being established. Once this is done, the monitored parameters are evaluated to determine typical data points and ranges for the process parameters. The parameter and trending alarm limits initially established during Phase 1 can then be adjusted to more realistic and useful values based upon data from actual system operation. Once these alarm limits are established, they can be reported back to the command center and can be password protected at the controller to prevent inadvertent or intentional alteration of the limits without proper authorization from the vessel company, governmental regulator, or insurance carrier.

Phase 3 is the normal system operation in which the controller monitors the various process parameters and executes the commands received via the communication link. In particular, controller 202 monitors the process parameters and performs the trending and parameter analysis that was defined during Phase 1. Upon detecting that a monitored parameter trend has fallen outside of its associated alarm limits, the controller sends an alert to the command center 212 along with a dump of all relevant data stored within the controller. If programmed to do so, the controller can also take corrective action, such as by increasing or decreasing system flow rates or even bypassing the separation system 10 altogether and discharging the bilge or ballast water directly overboard.

In this regard, alarm limits can be established for water volumes within the bilge and ballast tanks. These alarm limits can include a first high water level point which results in an alert being sent to the ship's engineer and the command center 212. Based on this notification, the ship's engineer or command center can determine whether processing through separation system 10 should be bypassed to decrease the water volumes within the ship. If so, then one or more bypass devices (such as pump 176 and valve 178 of FIG. 2) can be actuated either manually or via controller 202 to pump excess water overboard. A second high water level point can also be established which can be used by controller 202 to automatically start the bypass operation. Of course, the setpoints can be adjusted either manually or automatically based upon sea conditions so that, for example, in a high sea state the high water level alarm limits can be deactivated for a period of time if it is determined that a higher water level within the bilge or ballast tanks is desired.

The normal system operation also includes monitoring by controller 202 for remote commands received from the command center 212 via the communication unit 204. These commands can include a password or other authorization that is checked by the controller 202. Assuming proper authorization, the controller executes the command and thereafter confirms successful execution back to the command center.

Figure 14:
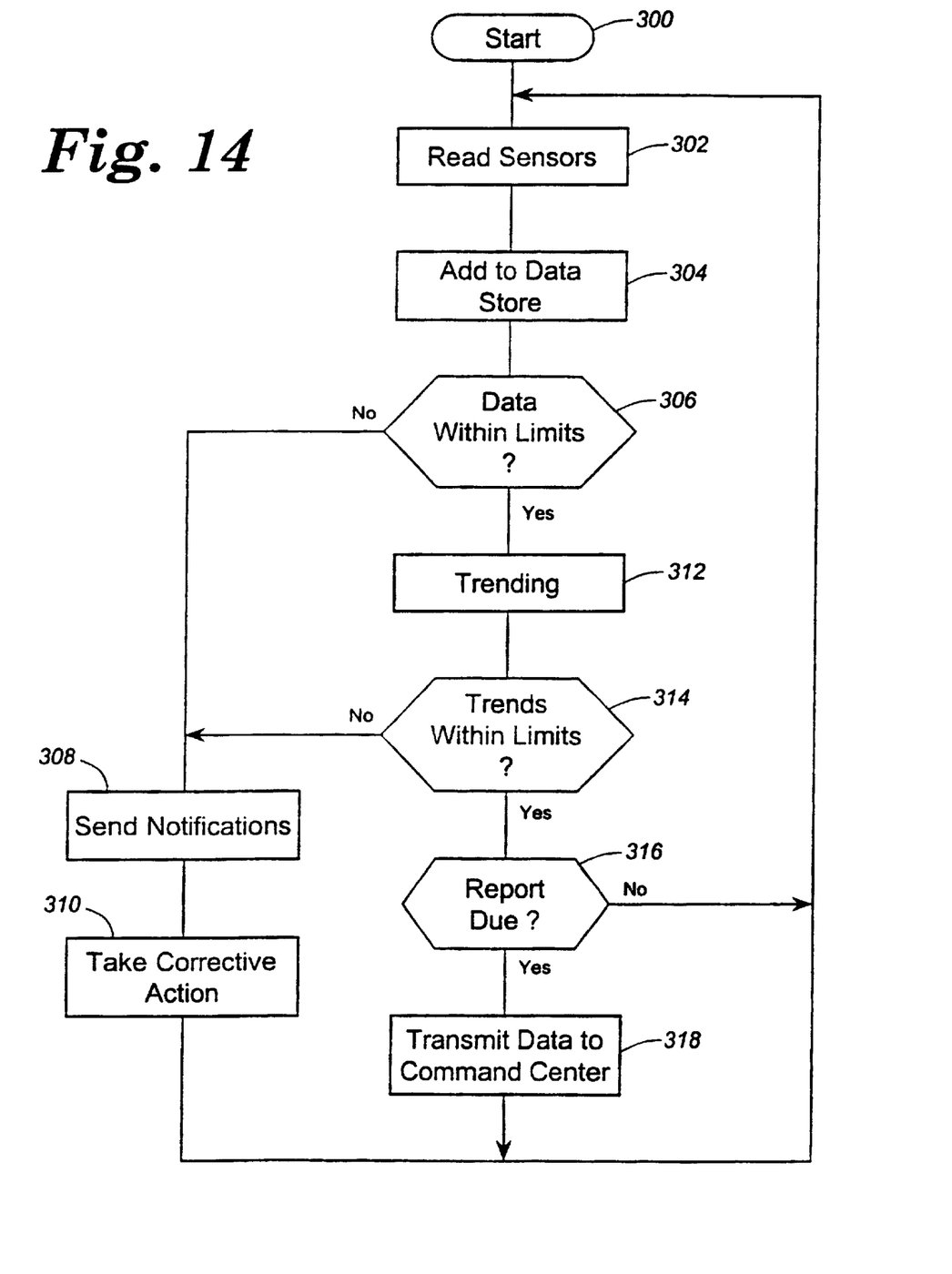
FIG. 14 is a flow chart depicting the process used by the system of FIG. 1 to monitor, analyze, and report data related to operation of the separation system of FIG. 2.

Referring now to FIG. 14, the process utilized by controller 202 for monitoring the various system parameters will now be described in greater detail. Beginning from start block 300, the first step is for the controller to initially read the data from the various meters and other sensors utilized by separation system 10. This is indicated at block 302. Then, at block 304, this data is added to the data store which can be implemented as a circular buffer in memory. Next, a check is made at block 306 to determine whether the data is within the established alarm limits. If not, the process flow moves to block 308 where an alert or other notification is sent to the ship's engineer and command center 212, after which the controller 202 automatically takes corrective action, if it is so programmed. The process flow then moves from block 310 and returns to block 302 for another iteration. If, at block 306, the data is within limits, the process flow moves to block 312 where trending of. the data occurs. The trended data is compared with its own alarm limits at block 314 and, if outside its associated limits, the process flow moves to block 308 and 310 for transmission of the proper notifications, as described above. If, at block 314, the trend data is within limits, the process flow moves to block 316 where check is made to determine if a periodic data report is due to be transmitted back to the command center. If so, the appropriate data is transmitted via the communication unit 204, as indicated at block 318. In either event, the flow returns to block 302 for another iteration.

Apart from the use of the data along with their associated alarm limits to determine leaks and abnormal operating conditions, the data monitored by the controller can also be used to set maintenance schedules for the various ship mechanical systems. For instance, if the trend data indicates that the amount of oil accumulation in a section of the ship begins to increase significantly after a particular period of time, then the maintenance schedules can be set on a shorter cycle to eliminate leaks before they become significant.

It will thus be apparent that there has been provided in accordance with the present invention a shipboard liquid separation system which achieves the aims and advantages specified herein. It will of course be understood that the foregoing description is of a preferred exemplary embodiment of the invention and that the invention is not limited to the specific embodiment shown. Various changes and modifications will become apparent to those skilled in the art. For example, although a high data rate satellite link is used in the illustrated embodiment, it will be appreciated that low data rates could be used and/or off-peak transmission times could be used to lower the cost of data transmission. In this regard, the system can be designed so that data transmission happens only upon occurrence of an event, such as crossing of an alarm limit by one of the monitored system parameters, or only at periodic times, such as once a week to provide historical, operational information. Moreover, communication between system 200 and command center 212 can be by other means, as will be known by those skilled in the art. Within separation system 10, instead of initially pumping bilge water into holding tank 12, the inlet end of intake line 30 can be submersed directly into the body of contaminated water in the ship's bilge. Also, standard flow valves can be utilized in place of the various one-way valves, in which case a check valve would also be placed in-line to prevent backflow. All such variations and modifications are intended to come within the scope of the appended claims.

What is claimed is:

1. A bilge/ballast water processing system for use on an ocean vessel to process contaminated bilge and/or ballast water contained onboard the ocean vessel and transmit related data to a remote facility, comprising:
    a separation system having a housing that includes an inlet and first and second outlets, said inlet being located internally within the vessel to receive bilge water and/or ballast water contained onboard the vessel, said separation system further including a pump coupled to said housing to provide a flow of the received water through said housing from said inlet to said first outlet, said separation system being operable to process the water flowing through said housing and supply separated contaminants to said second outlet;
    a data acquisition interface coupled to said separation system, said interface being operable to acquire data relating to processing of the bilge and/or ballast water by said separation system; and
    a communication unit coupled to said interface to receive the data acquired by said interface, said communication unit including an antenna and being operable to provide wireless transmission of the data to a remote facility via said antenna.

2. A system as defined in claim 1, wherein said housing comprises a separator having a plurality of flow restrictors spaced within said housing between said inlet and said first outlet.

3. A system as defined in claim 2, wherein said housing is disposed at an inclined angle with said inlet being located at a lower end of said housing and said first and second outlets being located at an upper end of said housing.

4. A system as defined in claim 2, wherein said separation system further comprises a coalescer having a housing that includes an inlet and first and second outlets, wherein said inlet of said coalescer is coupled to said first outlet of said separator and said pump is coupled to said separator and said coalescer to circulate the water through said separator and then through said coalescer.

5. A system as defined in claim 4, further comprising an accumulator coupled to said second outlets of said separator and said coalescer.

6. A system as defined in claim 1, wherein said housing comprises a coalescer having a coalescing element disposed in said housing between said inlet and said first outlet.

7. A system as defined in claim 1, wherein said separation system includes a sensor coupled to said interface to provide said interface with a signal indicative of a measurable parameter of said separation system, and wherein said interface includes a microprocessor operable under program control to process the signal as digital data and to provide said communication-unit with the digital data for transmission to the remote facility.

8. A system as defined in claim 7, wherein said microprocessor is operable under program control to provide an alert signal via said communication-unit when the digital data crosses an alarm limit.

9. A system as defined in claim 8, wherein said separation system further comprises a control element coupled to an output of said interface, said control element being operable upon actuation to cause a change in the operation of said separation system, wherein said microprocessor is operable under program control and in response to the digital data crossing the alarm limit to actuate said control element.

10. A system as defined in claim 1, wherein said separation system further comprises a plurality of sensors coupled to said interface to provide said interface with data values relating to operation of said separation system, wherein said interface is operable to transmit a subset of said data values to the remote facility using said communication unit.

11. A system as defined in claim 1, wherein said separation system further comprises a control element that is operable upon actuation to cause a change in the operation of said separation system, said interface further comprising a system control interface having an input coupled to said communication-unit and an output coupled to said control element, wherein said communication unit is operable to receive commands from the remote facility and said system control interface is operable in response to receiving a selected command from said communication unit to actuate said control element.

12. A system as defined in claim 1, further comprising a global positioning system coupled to said interface, wherein said interface is operable to receive data indicative of the ocean vessel's global position and is operable via said communication unit to report the global position to the remote facility along with data from said separation system.

13. A system as defined in claim 1, wherein said interface is operable to receive data indicative of the flow rate of the water through said separation system and wherein said interface is operable to send an alert to the remote facility via said transmitter unit when the flow rate falls outside a pre-established range of values.

14. A system as defined in claim 1, wherein said separation system further includes an oil accumulator having a level sensor coupled to said interface to provide said interface with a signal indicative of the amount of oil in said oil accumulator, wherein said interface is operable to send an alert when the amount of oil in said oil accumulator exceeds a preestablished value.

15. A system for use on an ocean vessel to process contaminated water and transmit related data to a remote facility, comprising:
- a separation system having a housing that includes an inlet and first and second outlets, said separation system further including a pump coupled to said housing to provide a flow of contaminated water through said housing from said inlet to said first outlet, said separation system being operable to process contaminated water flowing through said housing and supply separated contaminants to said second outlet;
- a data acquisition interface coupled to said separation system, said interface being operable to acquire data relating to processing of the contaminated water by said separation system;
- a transmitter unit coupled to said interface to receive the data acquired by said interface, said transmitter unit including an antenna and being operable to provide wireless transmission of the data to a remote facility via said antenna;
- a global positioning system coupled to said interface, wherein said interface is operable to receive data indicative of the ocean vessel's global position and is operable via said transmitter unit to report the global position to the remote facility along with data from said separation system; and
- a controller for said separation system and an electrically-operable bypass valve coupled to route the contaminated water around said separation system such that the contaminated water does not pass through said housing, said controller including said interface and being electrically coupled to said bypass valve to control operation of said valve, said controller being operable to monitor the ocean vessel's global position using said global positioning system and being operable to inhibit or permit activation of said bypass valve in accordance with the ocean vessel's global position.

16. A system as defined in claim 15, wherein said controller includes position data that identifies protected waters and wherein said controller is operable to compare the ocean vessel's global position with said position data and to inhibit operation of said bypass valve if the ocean vessel is located in protected waters.

* * * * *